US00PP21681P2

(12) United States Plant Patent

Sakazaki

(10) Patent No.: US PP21,681 P2

(45) Date of Patent: Jan. 25, 2011

(54) *HELIOTROPE* PLANT NAMED 'USHTRP0303'

(50) Latin Name: ***Heliotropium amplexicaule*×*Heliotropium leiocarpum***

Varietal Denomination: USHTRP0303

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/653,196

(22) Filed: Dec. 9, 2009

(51) Int. Cl.
*A01H 5/00* (2006.01)

(52) U.S. Cl. ..... Plt./438

(58) Field of Classification Search ..... Plt./438
See application file for complete search history.

*Primary Examiner*—Annette H Para

(74) *Attorney, Agent, or Firm*—C. A. Whealy

(57) ABSTRACT

A new and distinct cultivar of *Heliotrope* plant named 'USHTRP0303', characterized by its upright to outwardly spreading plant habit; vigorous growth habit; freely branching habit; freely flowering habit; fragrant violet-colored flowers; and good summer garden performance.

1 Drawing Sheet

Botanical designation: *Heliotropium amplexicaule*×*Heliotropium leiocarpum.*

Cultivar denomination: 'USHTRP0303'.

BACKGROUND OF THE INVENTION

The present invention relates to a new and distinct cultivar of *Heliotrope* plant, botanically known as *Heliotropium amplexicaule*×*Heliotropium leiocarpum* and hereinafter referred to by the name 'USHTRP0303'.

The new *Heliotrope* plant is a product of a planned breeding program conducted by the Inventor in Hikone, Shiga, Japan. The objective of the breeding program is to create new *Heliotrope* cultivars with good plant habit and attractive coloration.

The new *Heliotrope* plant originated from a cross-pollination made by the Inventor on Jun. 18, 2002 of *Heliotropium amplexicaule* 'Azure Skies', not patented, as the female, or seed, parent with and unnamed selection of *Heliotropium leiocarpum,* not patented, as the male, or pollen, parent. The new *Heliotrope* plant was discovered and selected by the Inventor as a single flowering plant with the progeny of the stated cross-pollination grown in a controlled greenhouse environment in Hikone, Shiga, Japan on Jul. 14, 2003.

Asexual reproduction of the *Heliotrope* plant by vegetative cuttings in Hikone, Shiga, Japan since Jul. 14, 2003, has shown that the unique features of this new *Heliotrope* plant are stable and reproduced true to type in successive generations.

SUMMARY OF THE INVENTION

Plants of the new *Heliotrope* have not been observed under all possible environmental conditions. The phenotype may vary somewhat with variations in environment such as temperature and light intensity without, however, any variance in genotype.

The following traits have been repeatedly observed and are determined to be the unique characteristics of 'USHTRP0303'. These characteristics in combination distinguish 'USHTRP0303' as a new and distinct cultivar of *Heliotrope:*

1. Upright to outwardly spreading plant habit.
2. Vigorous growth habit.
3. Freely branching habit.
4. Freely flowering habit.
5. Fragrant violet-colored flowers.
6. Good summer garden performance.

Plants of the new *Heliotrope* differ from plants of the female parent, 'Azure Skies', in the following characteristics:

1. Plants of the new *Heliotrope* are more mounding than and not as creeping as plants of 'Azure Skies'.
2. Plants of the new *Heliotrope* have darker-colored flowers than plants of 'Azure Skies'.
3. Flowers of plants of the new *Heliotrope* are more fragrant than plants of 'Azure Skies'.

Plants of the new *Heliotrope* differ from plants of the male parent selection in the following characteristics:

1. Plants of the new *Heliotrope* are more freely branching than plants of the male parent selection.
2. Plants of the new *Heliotrope* have smaller leaves than plants of the male parent selection.

Plants of the new *Heliotrope* can be compared to plants of *Heliotrope* 'Atlanta', disclosed in U.S. Plant Pat. No. 11,326. In side-by-side comparisons conducted in Bonsall, Calif., plants of the new *Heliotrope* differed from plants of 'Atlanta' in the following characteristics:

1. Plants of the new *Heliotrope* were more vigorous than and not as compact as plants of 'Atlanta'.
2. Flowers of plants of the new *Heliotrope* had yellow green-colored centers whereas flowers of plants of 'Atlanta' had purple-colored centers.
3. Flowers of plants of the new *Heliotrope* were more fragrant than flowers of plants of 'Atlanta'.

Plants of the new *Heliotrope* can also be compared to plants of *Heliotrope* 'Nagano', disclosed in U.S. Plant Pat. No. 14,077. In side-by-side comparisons conducted in Bonsall, Calif., plants of the new *Heliotrope* differed from plants of 'Nagano' in the following characteristics:

1. Plants of the new *Heliotrope* had lighter-colored flowers than plants of 'Nagano'.

2. Flowers of plants of the new *Heliotrope* had yellow green-colored centers whereas flowers of plants of 'Nagano' had purple-colored centers.
3. Flowers of plants of the new *Heliotrope* were more fragrant than flowers of plants of 'Nagano'.

BRIEF DESCRIPTION OF THE PHOTOGRAPHS

The accompanying colored photographs illustrate the overall appearance of the new *Heliotrope* plant, showing the colors as true as it is reasonably possible to obtain in colored reproductions of this type. Colors in the photographs may differ slightly from the color values cited in the detailed botanical description which accurately describe the actual colors of the new *Heliotrope* plant.

The photograph at the bottom of the sheet comprises a side perspective view of a typical flowering plant of 'USHTRP0303' grown in a container.

The photograph at the top of the sheet is a close-up view of typical flowers and leaves of 'USHTRP0303'.

DETAILED BOTANICAL DESCRIPTION

Plants used for the aforementioned photographs and following description were grown under conditions which closely approximate commercial production conditions during the autumn in 12.5-cm containers in an outdoor nursery in Bonsall, Calif. During the production of the plants, day temperatures ranged from 18° C. to 38° C., night temperatures ranged from 9° C. to 18° C. and light levels ranged from 7,000 to 10,000 foot-candles. Plants were pinched one time and were seven weeks old when the photographs and description were taken. In the following description, color references are made to The Royal Horticultural Society Colour Chart, 2007 Edition, except where general terms of ordinary dictionary significance are used.

Botanical classification: *Heliotropium amplexicaule*×*Heliotropium leiocarpum. 'USHTRP*0303'.

Parentage:

*Female parent.*—*Heliotropium amplexicaule* 'Azure Skies', not patented.

*Male parent.*—Unnamed selection of *Heliotropium leiocarpum,* not patented.

Propagation:

*Type cutting.*—Vegetative tip cuttings.

*Time to initiate roots, summer.*—About four days at temperatures ranging from 17° C. to 29° C.

*Time to initiate roots, winter.*—About six days at temperatures ranging from 17° C. to 21° C.

*Time to produce a rooted plant, summer.*—About 22 days at temperatures ranging from 17° C. to 29° C.

*Time to produce a rooted plant, winter.*—About 25 days at temperatures ranging from 17° C. to 21° C.

*Root description.*—Medium in thickness, fibrous; white in color.

*Rooting habit.*—Freely branching; medium in density.

Plant description:

*Form.*—Upright to outwardly spreading plant habit; inverted triangle; freely branching habit with about six lateral branches per plant each primary lateral developing two to three secondary and tertiary laterals, pinching enhances lateral branch development; vigorous growth habit.

*Plant height.*—About 34 cm.

*Plant width.*—About 33 cm by 50 cm.

*Lateral branch description.*—Length: About 31 cm. Diameter: About 5 mm. Internode length: About 4 cm to 4.5 cm. Strength: Strong, flexible. Texture: Pubescent; slightly viscid. Color: Close to 146B.

Foliage description:

*Arrangement.*—Opposite, simple.

*Length.*—About 6 cm.

*Width.*—About 3.1 cm.

*Shape.*—Lanceolate.

*Apex.*—Acute; recurved with development.

*Base.*—Obtuse.

*Margin.*—Entire, sinuate.

*Texture, upper and lower surfaces.*—Pubescent.

*Venation pattern.*—Pinnate; arcuate.

*Color.*—Developing leaves, upper and lower surfaces: Close to 146B. Fully expanded leaves, upper surface: Close to 147A; venation, close to 146C. Fully expanded leaves, lower surface: Close to 147B; venation, close to 146D.

*Petioles.*—Length: About 1.7 cm. Diameter: About 3 mm. Texture, upper and lower surfaces: Pubescent. Color, upper and lower surfaces: Close to 146C.

Flower description:

*Flower arrangement, form and habit.*—Small actinomorphic funnelform flowers arranged in compact terminal helicoid cymes; three to four cymes per stem apex; freely flowering habit with about 58 flowers per inflorescence; flowers face mostly upright to outwardly to curling backwards depending on position in helicoid cyme; flowers sessile.

*Natural flowering season.*—Under greenhouse conditions, plants begin flowering about seven weeks after planting. Under outdoor conditions, plants begin flowering during the spring and flower continuously until frost in California.

*Flower longevity on the plant.*—Longevity of individual flowers is highly dependent on environmental conditions; flowers typically last about three to four days on the plant; flowers persistent.

*Fragrance.*—Strongly fragrant; sweet, pleasant, violet-like.

*Flower buds.*—Length. About 7 mm. Diameter. About 3 mm. Shape. Ovate. Color: Close to 85B.

*Flower diameter.*—About 1 cm.

*Flower depth (height).*—About 8 cm.

*Inflorescence diameter.*—About 5 cm by 5.5 cm.

*Inflorescence height.*—About 4 cm to 5.5 cm.

*Petals.*—Arrangement: Single whorl of five petals, petals fused at the base into a narrow tube. Lobe length: About 3 mm. Lobe width: About 3 mm. Shape: Obovate. Apex: Rounded. Margin: Entire, undulate and wrinkled. Lobe and tube texture, upper and lower surfaces: Smooth, glabrous; velvety. Throat texture: Pubescent. Color: When opening, upper surface: Close to 85B. When opening, lower surface: Close to 85C to 85D. Fully opened, upper surface: Close to 85B; towards the base, close to NN155B; color does not fade with development. Fully opened, lower surface: Close to 85B to 85C; color does not fade with development. Throat: Close to 151B. Tube: Close to 150B.

*Sepals.*—Arrangement: Single whorl of five sepals, fused at the base; star-shaped calyx. Length: About 3 mm. Width: About 1 mm. Shape: Lanceolate. Apex: Acute. Margin: Entire. Texture, upper surface:

Smooth, glabrous. Texture, lower surface: Pubescent. Color, upper and lower surfaces: Close to 146B.

*Peduncles.*—Length: About 3.5 cm to 5 cm. Diameter: About 2 mm. Aspect: Erect to about 45° from the lateral stem axis. Strength: Strong, flexible. Texture: Pubescent. Color: Close to 146B.

*Reproductive organs.*—Stamens: Quantity per flower: About five. Filament length: Less than 1 mm. Filament color: Close to 157A. Anther length: About 2 mm. Anther shape: Oval. Anther color: Close to 157C. Pollen amount: None observed. Pistils: Quantity per flower: One. Pistil length: About 1.5 mm. Stigma shape: Round. Stigma color: Close to 144B. Style length: About 1 mm. Style color: Close to 144B. Ovary color: Close to 144B.

*Seeds/fruits.*—Seed and fruit development have not been observed.

Disease/pest resistance: Plants of the new *Heliotrope* have not been noted to be resistant to pathogens and pests common to *Heliotrope.*

Garden performance: Plants of the new *Heliotrope* have been observed to have good summer garden performance and to tolerate temperatures from about 1° C. to about 40° C.

It is claimed:

1. A new and distinct *Heliotrope* plant named 'USHTRP0303' as illustrated and described.

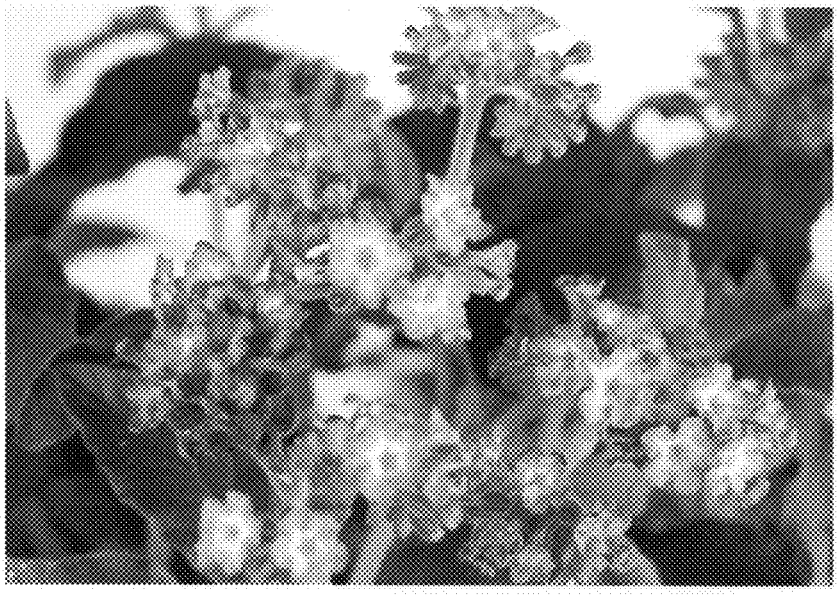
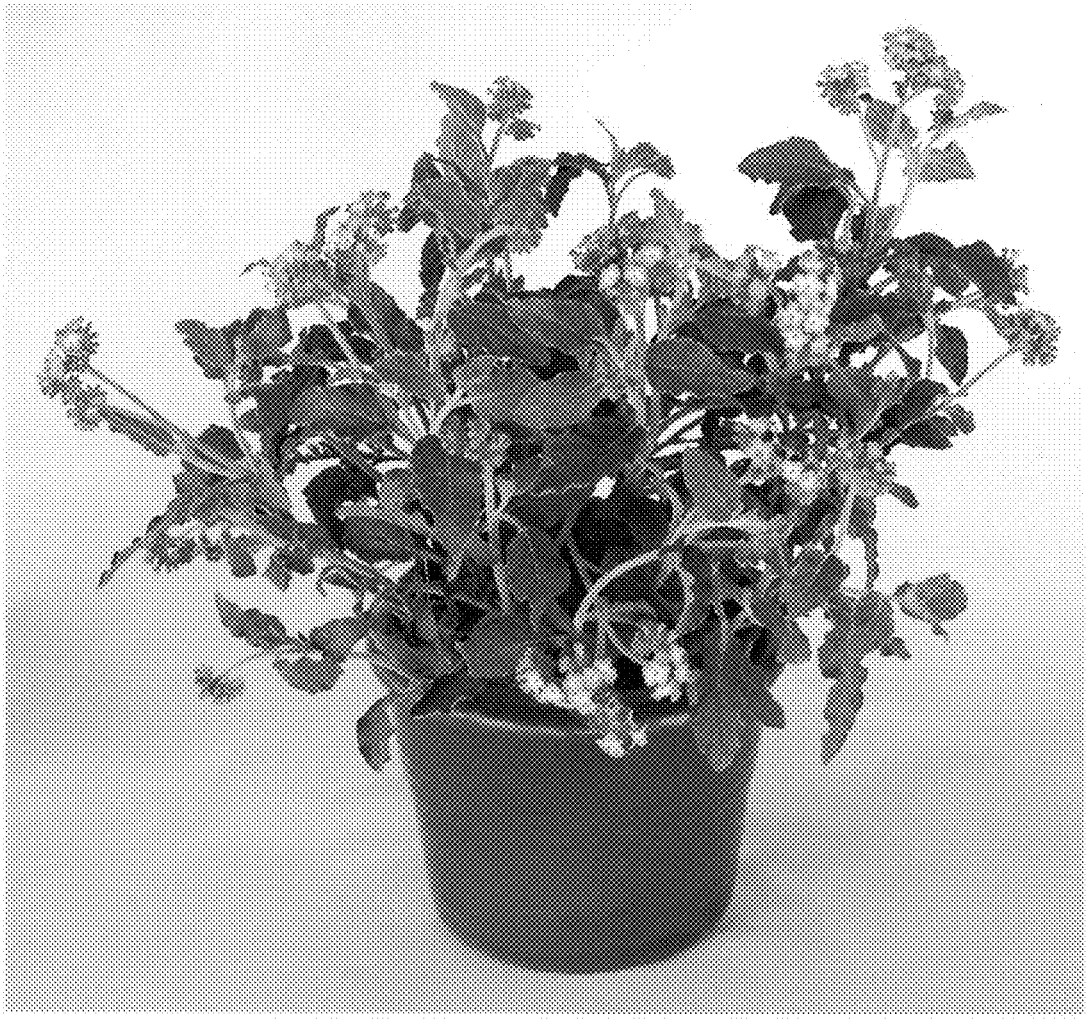

* * * * *